United States Patent [19]

Schröder et al.

[11] Patent Number: 5,767,325
[45] Date of Patent: Jun. 16, 1998

[54] PREPARATION OF ENOL ETHERS

[75] Inventors: Jürgen Schröder; Stefan Böck, both of Ludwigshafen; Klaus Ebel, Lampertheim, all of Germany

[73] Assignee: BASF Aktiengesellschaft, Ludwigshafen, Germany

[21] Appl. No.: 755,299

[22] Filed: Nov. 22, 1996

[30] Foreign Application Priority Data

Nov. 29, 1995 [DE] Germany .................. 195 44 450.7

[51] Int. Cl.$^6$ .................................................. C07C 41/28
[52] U.S. Cl. .................................................. 568/691
[58] Field of Search ........................... 568/691; 502/77

[56] References Cited

U.S. PATENT DOCUMENTS

| 1,902,169 | 3/1933 | Herrmann et al. . |
| 5,100,852 | 3/1992 | Arntz et al. ............... 502/77 |

FOREIGN PATENT DOCUMENTS

| A 3535128 | 4/1987 | Germany . |
| A 3722891 | 1/1989 | Germany . |
| A 3804162 | 8/1989 | Germany . |
| 706712 | 4/1954 | United Kingdom . |

OTHER PUBLICATIONS

Banciu et al, Chem. Abstracts, vol. 94 (19): 156,241f, May 11, 1981, A laboratory method for synthesis of isopropenyl methyl ether, p. 599, col. 2.

Cerveny et al, J. Chem. Tech. Biotechnol., 1993, vol. 58, pp. 212–214, Catalytic Splitting of Alcohols to Unsaturated Ethers.

*Primary Examiner*—Gary Geist
*Assistant Examiner*—Sreeni Padmanabhan
*Attorney, Agent, or Firm*—John H. Shurtleff

[57] ABSTRACT

A process for the preparation of enol ethers of the general formula I

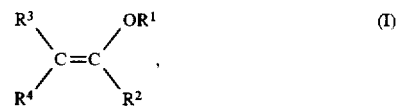

in which $R^1, R^2, R^3, R^4, R^5$ denote $C_1$–$C_{20}$ alkyl, $C_1$–$C_{20}$ alkenyl, or $C_7$–$C_{20}$ phenylalkyl, $R^2, R^3, R^4$ denote hydrogen, aryl, cyano, —COOR$^5$, $C_1$–$C_{12}$ alkyl monosubstituted to trisubstituted or interrupted by —COOR$^5$, —C=O, cyano, or $C_1$–$C_{12}$ alkoxy, $C_1$–$C_{12}$ alkyl monosubstituted to trisubstituted by —COOR$^5$, —C=O, cyano, or $C_1$–$C_{12}$ alkyl, or $C_7$–$C_{20}$ phenylalkyl and $R^2$ and $R^4$ or $R^3$ and $R^4$ together form a $C_3$–$C_{10}$ alkylene chain or a $C_2$–$C_{20}$ alkylidene chain, from acetals or ketals.

10 Claims, No Drawings

PREPARATION OF ENOL ETHERS

The present invention relates to a process for the preparation of enol ethers by the reaction of acetals/ketals in the gas phase over highly porous oxidic heterogeneous catalysts.

DE-A 3,535,128 reveals the catalytic dealkoxylation of geminate dialkoxy compounds for the preparation of vinyl ethers on ZSM5- and mordenite-type zeolites, which exhibit a specific $Na_2O/Al_2O_3$ ratio of 1:1.05 (±0.25). Using these catalysts a selectivity of 90% is attained for example in the synthesis of methoxypropenes from acetone dimethylacetal, at a conversion of 93%.

DE-A 3,722,891 reveals a process for the preparation of vinyl ethers from acetals over boron and/or iron silicate zeolites in their acidic H forms. These catalysts deactivate however within a few hours due to coking and thus demand frequent interruptions in production for regeneration of the catalyst.

DE-A 3,804,162 reveals a process for the preparation of enol ethers from acetals using phosphates having zeolite structure, precipitated phosphates of the elements boron, zirconium, cerium, iron, boric acid, or phosphoric acid on support material and/or acid undoped metal oxides as catalysts. Although all of these highly acidic catalysts show high selectivities, their on-stream times of only a few hours are inadequate for economical operation of the process.

Chemical Abstracts, Vol. 94(19);156,241 et seq reveals a process for the preparation of 2-methoxypropene by the reaction of 2,2-dimethoxypropane over non-acidic α-aluminum oxide sold by Alcoa having low porosity estimated to be from 10 to 15%, approximately. This catalyst attains at 50° C. a conversion of only 90% and deactivates rapidly within a few hours. Using highly porous acidic aluminum oxide ("acid alumina") of the type PS 100, which is not specified further (manufacturer not named), acetone/methanol or the secondary product hexamethylbenzene is formed exclusively.

It is thus an object of the present invention to overcome the aforementioned drawbacks.

Accordingly, we have found a novel and improved process for the preparation of enol ethers of the general formula I

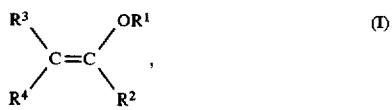

in which $R^1, R^2, R^3, R^4, R^5$ denote $C_1-C_{20}$ alkyl, $C_1-C_{20}$ alkenyl, or $C_7-C_{20}$ phenylalkyl, $R^2, R^3, R^4$ denote hydrogen, aryl, cyano, —$COOR^5$, $C_1-C_{12}$ alkyl monosubstituted to trisubstituted or interrupted by —$COOR^5$, —C=O, cyano, or $C_1-C_{12}$ alkoxy, $C_1-C_{12}$ alkyl monosubstituted to trisubstituted by —$COOR^5$, —C=O, cyano, or $C_1-C_{12}$ alkyl, or $C_7-C_{20}$ phenylalkyl and $R^2$ and $R^4$ or $R^3$ and $R^4$ together form a $C_3-C_{10}$ alkylene chain or a $C_2-C_{20}$ alkylidene chain, from acetals or ketals of the general formula II

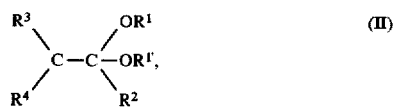

in which $R^1$, $R^2$, $R^3$, and $R^4$ have the aforementioned meanings and $R^{1'}$ has the same meanings independently of $R^1$, in the gas phase at temperatures ranging from 100° to 550° C. and under a pressure of from 0.001 to 5 bar over heterogeneous catalysts, wherein the heterogeneous catalyst used is a highly porous Group IIa, Group IIIa, Group IVa, Group IIb and/or Group IVb oxide having a pH of from 7 to 14, a porosity of from 40 to 80%, and a surface area (BET) of from 0.5 to 250 m²/g.

The process of the invention can be carried out as follows:

The acetal or ketal II can be caused to react by contacting the same with a highly porous, oxidic heterogeneous catalyst in a fixed-bed reactor, a fluid-bed reactor, or a derived reactor form, eg. a riser reactor, at temperatures ranging from 100° to 550° C., preferably from 180° to 400° C. and more preferably from 200° to 350° C. and under a pressure of from 0.001 to 5 bar, preferably from 0.01 to 2 bar, more preferably from 0.1 to 1 bar and most preferably under standard pressure (atmospheric pressure) and optionally in the presence of an inert gas such as nitrogen and/or argon.

The process may be carried out by passing the starting materials II, having been heated to the temperature of reaction, over the catalyst after this has also been heated to the temperature of reaction. The mixture leaving the reaction chamber can be condensed and fractionally distilled.

If a particularly high conversion is desired or little or no educt (ketal or acetal) should be present in the effluent formed, any by-product formed, usually the corresponding ketone and an increased amount of alcohol, can be separated during the following distillation and, if desired, ketalized or acetalized back to educt. If a particularly high selectivity is desired and consequently little or no by-product (ketone or aldehyde) should be present in the effluent formed, any educt present (ketal or acetal) can be separated during the following distillation and, if desired, used again as educt.

Suitable highly porous, oxidic heterogeneous catalysts are non-acidic Group IIa, Group IIIa, Group IVa oxides and also the Group IIb and Group IVb oxides and mixtures thereof, preferably magnesium oxide, aluminum oxide, silicon dioxide, zinc oxide and titanium dioxide and mixtures thereof and more preferably α-aluminum oxide, Γ-aluminum oxide, silicon dioxide and zinc oxide/Γ-aluminum oxide and particularly α-aluminum oxide usually having a porosity of from 40 to 80%, preferably from 50 to 75% and more preferably from 60 to 70%.

The porosity is defined as the ratio of the volume of the pores of a solid material to the total volume, i.e. the volume of the pores plus the volume of the solid framework.

The porosity can be determined for example as follows:

In a weighing boat, from 15 to 20 g of the sample of the porous solid material are weighed. The sample weight in grams thus determined is designated as $m_1$. This sample is placed in a suitable flask equipped with a vacuum connector and a mounted pressure-tight drip funnel, e.g., a two-necked flask (round-bottom flask or tapered flask) or a so-called "Schlenk" flask, i.e. a round-bottom flask having a closable gas/vacuum connector and which has been provided with a pressure-tight drip funnel, and evacuated to a pressure of 1 torr or less over a period of approximately 5 minutes using a vacuum pump. The drip funnel is closed during the evacuation and was previously filled with sufficient distilled water to ensure that after the evacuation phase the sample in the evacuated flask can be completely covered by water. The flask is then ventilated completely and the sample left to stand under water for one minute. The sample is afterwards separated from excess water, for example by the use of a suitable screen or a filter. In the case of porous filtering media, for example filter paper or glass frits, care should be taken to ensure that they are moistened, as otherwise water is again withdrawn from the sample. The sample must then be freed from adhering water drops, for example by scimming the shaped articles with a moistened filter paper in a Petri dish or by tapping the screen or the filter on a firm surface.

The sample weighing $m_2$ in grams is now placed in a pycnometer of appropriate capacity V in milliliters and the total weight of the pycnometer containing the sample is then determined. This total weight in grams is designated $m_3$. The pycnometer is now filled up with water. In the case of certain shaped articles, for example rings, bubbles of air can form at certain points on the shaped bodies—for example in the inner cavity of rings. These bubbles of air should be removed by carefully tapping the pycnometer on a hard surface for example. The weight of the pycnometer filled with sample and water in grams is determined and noted as $m_4$.

The porosity, in percent, is calculated therefrom as follows:

$$\text{Porosity} = \frac{m_3 - m_2 - m_1}{(V - (m_4 - m_3))100} \ [\%]$$

The acidity of the highly porous, oxidic heterogeneous catalysts generally corresponds to a pH of from 7 to 14, preferably from 8 to 14 and more preferably from 11 to 14. For Γ-aluminum oxide and silicon dioxide this acidity advantageously corresponds to a pH of from 11 to 14 and for zinc oxide and α-aluminum oxide it advantageously corresponds to a pH of from 7 to 12 and preferably from 8 to 11.

The acidity can be tested as follows:

10 g of the catalyst are ground and suspended in 100 mL of distilled or demineralized water having a pH of 7. The pH of the suspension is afterwards measured until a stable value is attained. Reaching a stable pH can take some time, i.e., up to about one hour.

The surface area (BET) [Chem. Ing. Techn. 35 (1963) pp. 586 to 589] of the highly porous, oxidic heterogeneous catalysts is usually from 0.5 to 250 $m^2/g$, preferably from 0.5 to 200 $m^2/g$ and more preferably from 0.6 to 50 $m^2/g$.

These catalysts can be produced by well-known methods, such as the precipitation of suitable precursor compounds or of mixtures of suitable precursor compounds followed by dyring and/or calcination. Mixed oxide catalysts can be prepared for example by coprecipitation from a solution that contains all precursor components in dissolved form, by precipitation or impregnation of dissolved components on to a solid body that contains other components of the mixed oxide and subsequent drying and/or calcination, or alternatively by physically mixing suitable solid precursor components. For the purpose of setting the porosity, auxiliaries, for example totally combustible materials, which are decomposed and converted to gaseous compounds during calcination, can be added at an appropriate point to form a predetermined pore structure. During the catalyst synthesis other generally known process steps can be accomplished, such as further drying, calcination, impregnation, purification, or shaping steps. The physical shape of the catalyst can be adjusted to the control requirements of the reaction and the conditions existing in the reactor used. The highly porous, oxidic catalysts can be used in the form of shaped articles, for example extrudates, pellets, rings, balls, Berl saddles, in the form of the hi-flow elements sold by Rauscher or pellets provided with a number of parallel passageways, or in any other suitable form.

Numerous suitable oxides are commercially available and are frequently sold as catalyst supports.

Catalysts exhibiting in the original state unduly high acidities, such as most commercially available Γ-aluminum oxides and silicon dioxides having the required porosity and surface area (BET) can be adjusted to the desired acidity by the addition of alkaline compounds, such as sodium hydroxide, triethylamine, hexamethylenediamine, etc. The addition of alkaline compound can take place for example by the known process of ion exchange or by impregnation of the unduly acidic catalyst with an alkaline compound or a solution thereof in a suitable solvent, for example by impregnation with an aqueous sodium hydroxide solution or alternatively by means of another solution of a compound of an alkali metal element or alkaline earth metal element, of an organic amine or some other suitable compound followed, if advantageous, by drying, e.g., at a temperature of 20° to 150° C. and/or calcination, eg, at a temperature of 150° to 1500° C.

Normally, however a catalyst consisting of α-aluminum oxide having a porosity of more than 60%, an acidity equivalent to a pH of at least 7 and a surface area (BET) of at least 0.5 $m^2/g$ is a particularly preferred catalyst for carrying out the reaction with virtually quantitative conversion and nearly 100% strength selectivity at temperatures ranging from 200° to 350° C. under standard or reduced pressure.

The substituents $R^1$, $R^1$, $R^2$, $R^3$, $R^4$ and $R^5$ in the compounds I and II have the following meanings:

$R^1, R^1, R^2, R^3, R^4, R^5$ independently, preferably $R^1 = R^1$.

$C_1-C_{20}$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, preferably $C_1-C_4$ alkyl such as methyl, ethyl, n-propyl, isopropyl, n-butyl, isobutyl, sec-butyl and tert-butyl and more preferably $C_1-C_3$ alkyl such as methyl, ethyl, n-propyl and isopropyl.

$C_7-C_{20}$ phenylalkyl, preferably $C_7-C_{12}$ phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl and more preferably benzyl, 1-phenethyl and 2-phenethyl.

$C_2-C_{20}$ alkenyl such as vinyl, propenyl, isopropenyl, and butenyl, $R^2, R^3, R^4$ hydrogen, aryl such as phenyl, 1-naphthyl, 2-naphthyl, 1-anthryl, 2-anthryl and 9-anthryl, preferably phenyl, 1-naphthyl and 2-naphthyl and more preferably phenyl.

cyano, $COOR^5$, $C_1-C_2$ alkyl monosubstituted to trisubstituted or interrupted by $-COOR^5$, $-C=O$, cyano, or $C_1-C_{12}$ alkoxy such as methyl acetate, ethyl acetate, acetyl, cyanomethyl, cyanoethyl, methoxymethyl, methoxyethyl, ethoxymethyl, ethoxyethyl, methoxypropyl and ethoxypropyl.

aryl monosubstituted to trisubstituted by $C_1-C_{12}$ alkyl, $C_1-C_{12}$ alkoxy, halogen, or cyano such as o-chlorophenyl, p-chlorophenyl, 2,4-dichlorophenyl, o-cyanophenyl, p-cyanophenyl, 2,4-dicyanophenyl, o-methoxyphenyl, p-methoxyphenyl, o-ethoxyphenyl and p-ethoxyphenyl,—aryl monosubstituted to trisubstituted by $C_1-C_{12}$ alkyl, $C_1-C_{12}$ alkoxy, halogen, or $C_1-C_{12}$ alkyl such as o-chlorobenzyl, p-chlorobenzyl, 2,4-dichlorobenzyl, o-cyanobenzyl, p-cyanobenzyl, 2,4-dicyanobenzyl, o-methoxybenzyl, p-methoxybenzyl, o-ethoxybenzyl and p-ethoxybenzyl, o-chlorophenylethyl, p-chlorophenylethyl, 2,4-dichlorophenylethyl, o-cyanophenylethyl, p-cyanophenylethyl, 2,4-dicyanophenylethyl, o-methoxyphenylethyl, p-methoxyphenylethyl, o-ethoxyphenylethyl, and p-ethoxyphenylethyl and $R^2$ and $R^4$ or $R^3$ and $R^4$ together form a $C_3$–$C_{10}$ alkylene chain such as $(CH2)3$, $(CH_2)_4$, $(CH_2)_5$, $(CH_2)_6$, $(CH_2)_7$, $(CH_2)_8$, $(CH_2)_9$ and $(CH_2)_{10}$, preferably $(CH_2)_3$, $(CH_2)_4$, $(CH_2)_5$ and $(CH_2)_6$ and more preferably $(CH_2)_3$, $(CH_2)_4$ and $(CH_2)_6$.

$R^3$ and $R^4$ together form a $C_2$–$C_{20}$ alkylidene chain such as ethylidene, propylidene, and isopropylidene.

Suitable starting compounds II are for example 1,1-dimethoxyethane, 1,1-dimethoxypropane, 2,2-dimethoxypropane, 1,1-dimethoxybutane, methyl 2,2-dimethoxypropionate, methyl 3,3-dimethoxypropionate, 1,1-diethoxyethane and 1,1-diethoxypropane.

Enol ethers, and especially vinyl ethers are used in the preparation of certain homopolymers and copolymers which are employed in the manufacture of paints and adhesives and also as auxiliaries in the textile and leather industries. Furthermore, enol ethers serve as valuable intermediates for organic syntheses, eg. for Diels-Alder-reactions, for the preparation of glutaric dialdehydes, Γ-pyran, Γ-picoline, and also active substances.

EXAMPLES

TABLE 1

Catalysts Used

| Catalyst | Composition | Porosity [%] | Surface Area (BET) [m²/g] | pH |
|---|---|---|---|---|
| A | 90 wt % ZnO, 10 wt % γ-Al$_2$O$_3$ | 54 | 60 | 10.61 |
| B | >99 wt % α-Al$_2$O$_3$ | 69.2 | 0.9 | 8.23 |
| C | >99 wt % SiO$_2$ | 67.1 | 140 | 5.58 |
| D | >99 wt % γ-Al$_2$O$_3$ | 66.1 | 180 | 8.67 |
| E | >99 wt % α-Al$_2$O$_3$ | 68.2 | 1.2 | 8.52 |
| F | >99 wt % α-Al$_2$O$_3$ | 63.6 | 4.1 | 10.33 |
| G | >99 wt % α-Al$_2$O$_3$ | 62.7 | 0.5 | 9.93 |

Example 1

30 ml/h of 2,2-dimethoxypropane were evaporated and passed through a fixed bed reactor heated to 300° C. and packed with 60 ml of catalyst A. The reaction gases were subsequently condensed and distilled. There were obtained 16.9 g (96%) of 2-methoxypropene per hour. No catalyst deactivation was observed.

Example 2

60 ml/h of 2,2-dimethoxypropane were evaporated and passed through a fixed bed reactor heated to 220° C. and packed with 30 ml of catalyst B. The reaction gases were subsequently condensed and distilled. There were obtained 34.2 g (97%) of 2-methoxypropene per hour. No catalyst deactivation was observed.

Example 3

480 ml/h of 2,2-dimethoxypropane were evaporated and passed through a fixed bed reactor heated to 300° C. and packed with 60 ml of catalyst B. The reaction gases were then condensed and distilled. There were obtained 265.2 g (94%) of 2-methoxypropene per hour. No catalyst deactivation was observed. The example showed the high space velocity achieved by the catalyst B.

Example 4

15 ml/h of 2,2-dimethoxypropane were evaporated and passed through a fixed bed reactor heated to 300° C. and packed with 60 ml of catalyst C. The reaction gases were subsequently condensed and analyzed by gas chromatography. The effluent contained 22% by area of methanol, 45% by area of acetone and 2% by area of 2-methoxypropene.

the precentages "by area" stated here and below are the percentages by area calculated after integration of the gas chromatographs serving for the analysis of the effluent. The example showed that the untreated catalyst C exhibits under these conditions with quantitative conversion (no 2,2-dimethoxypropane detected) only very poor selectivity toward the desired product 2-methoxypropene. Instead, the ketal is almost completely degraded to the ketone and alcohol. No catalyst deactivation was observed.

Examples 5 to 8

The silicon dioxide catalyst C from the previous experiment was taken out, suspended in 100 ml water, admixed with 10 ml of an aqueous solution containing in each case the amount of sodium hydroxide stated in the following table, and, following an impregnation time of two hours at 100° C., dried in a water-jet vacuum and used in the next experiment.

The Examples 5 to 8 listed in Table 2 were carried out in a manner similar to that described in Example 4. 30 ml of 2,2-dimethoxypropane were evaporated, per hour. In no instance was catalyst deactivation observed.

TABLE 2

| Ex. No. | NaOH [mg] | pH | Methanol [% by area] | Acetone [% by area] | 2-Methoxy propene [% by area] | 2,2-Dimethoxy propane [% by area] |
|---|---|---|---|---|---|---|
| 5 | 133 | 8.95 | 25 | 32 | 7 | 0 |
| 6 | 713 | 10.43 | 20 | 13 | 52 | 0 |
| 7 | 845 | 11.50 | 20 | 4 | 73 | 1 |
| 8 | 1706 | 12.22 | 17 | 1 | 65 | 16 |

Examples 5 to 8 show that the catalyst C which is non-selective in the original state becomes more selective by treatment with alkali: the content of the desired product 2-methoxypropene in the product stream rises constantly with the pH and the content of the by-product acetone falls constantly. Example 8 demonstrates that increasing alkali treatment decreases the activity of the catalyst, since unconverted educt is detected in significant amounts.

Example 9

30 ml/h of 2,2-dimethoxypropane were evaporated and passed through a fixed bed reactor heated to 300° C. and packed with 60 ml of the catalyst D. The reaction gases were subsequently condensed and analyzed by gas chromatography. The effluent contained 12% by area of methanol and 74% by area of acetone. The example demonstrates that the untreated catalyst D showed under these conditions with quantitative conversion (no 2,2-dimethoxypropane detectable) no selectivity toward the desired product 2-methoxypropene. Instead, the ketal was almost completely degraded to the ketone and the alcohol. No catalyst deactivation was observed.

Examples 10 to 12

The Γ-aluminum oxide catalyst D from the previous example was taken out, suspended in 100 ml water, admixed with 10 ml of an aqueous solution containing in each case the amount of sodium hydroxide stated in Table 3, following a period of two hours in a rotary evaporator at 100° C. dried in a water-jet vacuum and used in the next experiment.

Examples 10 to 12 were carried out in a manner similar to that described in Example 9. 30 ml /h of 2,2-dimethoxypropane were evaporated. In no instance was catalyst deactivation observed.

TABLE 3

| Ex. No. | NaOH [mg] | pH | Methanol [% by area] | Acetone [% by area] | 2-Methoxy propene [% by area] | 2,2-Dimethoxy propane [% by area] |
|---|---|---|---|---|---|---|
| 10 | 133 | 10.12 | 23 | 41 | 20 | 0 |
| 11 | 713 | 12.01 | 20 | 9 | 68 | 0 |
| 12 | 845 | 12.57 | 17 | 1 | 69 | 12 |

Examples 10 to 12 show that the catalyst D which is non-selective in the original state becomes more selective by treatment with alkali: the content of the desired product 2-methoxypropene in the product stream rises constantly with the pH and the content of the by-product acetone falls constantly. Example 12 demonstrates that increasing alkali treatment decreases the activity of the catalyst, since unconverted educt is detected in significant amounts.

Example 13

60 ml/h of 1,1-diethoxypropane were evaporated and passed through a fixed bed reactor heated to 300° C. and packed with 60 ml of the catalyst E. The reaction gases were subsequently condensed and analyzed by gas chromatography. The effluent contained 26% by area of ethanol, 64% by area of cis/trans 1-ethoxypropene and 1% by area of 1,1-diethoxypropane. No catalyst deactivation was observed.

Example 14

60 ml/h of methyl 2,2-dimethoxypropionate were evaporated and passed through a fixed bed reactor heated to 250° C. and packed with 60 ml of the catalyst E. The reaction gases were subsequently condensed and analyzed by gas chromatography. The effluent contained 14% by area of methanol, 82% by area of methyl 2-methoxyacrylate and 1% by area of methyl 2,2-dimethoxypropionate. No catalyst deactivation was observed.

Example 15

30 ml/h of 2,2-dimethoxypropane were evaporated and passed through a fixed bed reactor heated to 300° C. and packed with 60 ml of the catalyst F. The reaction gases were subsequently condensed and analyzed by gas chromatography. The effluent contained 20% by area of methanol, 1% by area of acetone, 77% by area of 2-methoxypropene and 1% by area of 2,2-dimethoxypropane. No catalyst deactivation was observed.

Example 16

30 ml/h of 2,2-dimethoxypropane were evaporated and passed up through a fixed bed reactor heated to 300° C. and packed with 60 ml of the catalyst G. The reaction gases were subsequently condensed and analyzed by gas chromatography. The effluent contained 14% by area of methanol, 2% by area of acetone, 52% by area of 2-methoxypropene, and 32% by area of 2,2-dimethoxypropane.

Examples 13, 14, and 15 show that variously suitable educts can be caused to react over different catalysts of the invention with quantitative or nearly quantitative conversion and a selectivity near to or equal to 100% toward the desired enol ethers. Example 16 demonstrates that a catalyst consisting of α-aluminum oxide having a surface area (BET) of 0.5 m$^2$/g exhibits a lower conversion than a catalyst consisting of α-aluminum oxide having a surface area (BET) of 0.9 m$^2$/g (catalyst B) or higher surface areas (BET) (catalysts E and F), i.e. it is less active.

Example 17

10 ml/h of 1,1-dimethoxy-3-methylbut-2-ene were evaporated and passed through a fixed bed reactor heated to 350° C. and packed with 60 ml of the catalyst B. The reaction gases were subsequently condensed and analyzed by gas chromatography. The effluent contained 13.3% by area of methanol and 84.0% by-area of 1-methoxy-3-methyl-1,3-butadiene (cis/trans mixture).

Example 18

2,2-Dimethoxy-4-methyl-3-pentene (56 g, approx. 90% strength) were passed through a fixed-bed reactor heated at 250° C. and packed with 35 ml of catalyst B over a period of 3 hours under a pressure of 30 mbar. The effluent was condensed in a cold trap and then distilled after the addition of a flake of KOH. The fraction boiling at 48°–52° C. (50 mbar) (a total of 41.5 g) contained 44% of 2-methoxy-4-methylpentadiene-1,3, 37% of 2-methyl-4-methoxypentadiene-1,3 (cis/trans mixture), 4% of 2-methoxy-4-methylpentadiene-1,4, 5% of starting material, and 8% of mesityl oxide, an impurity present in the starting material.

Example 19

2,2,4-Trimethoxy-4-methylpentane (70 g, approx. 95% strength) were passed through a fixed-bed reactor heated at 250° C. and packed with 35 ml of catalyst B over a period of 3 hours under a pressure of 30 mbar. The effluent was condensed in a cold trap and then distilled after the addition of a flake of KOH, under standard pressure conditions, in order to remove the methanol formed. The crude product contained 23% of 2-methoxy-4-methylpentadiene-1,3, 29% of 2-methyl-4-methoxypentadiene-1,3 (cis/trans mixture), 7% of 2-methoxy-4-methylpentadiene-1,4, and 35% of 2,4-dimethoxy-4-methyl-1-pentane.

Example 20

1,1-Dimethoxyhexane (158 g) were passed through a fixed-bed reactor heated at 350° C. and packed with 35 ml of catalyst B over a period of 4.5 hours under a pressure of 25 mbar. The effluent was condensed in a cold trap and then distilled after the addition of a flake of KOH. There was obtained 1-methoxy-1-hexene (111 g of cis/trans mixture) as a colorless liquid (bp 52° C./60 mbar) in a yield of 90%.

Example 21

1,1-Dimethoxyoctane (209 g) were passed through a fixed-bed reactor heated at 350° C. and packed with 35 ml of catalyst B over a period of 4 hours under a pressure of 25 mbar. The effluent was condensed in a cold trap and then distilled after the addition of a flake of KOH. There was obtained 1-methoxy-1-octene (164 g of cis/trans mixture) as a colorless liquid (bp 78° C./30 mbar) in a yield of 96%.

Example 22

1,1-Dimethoxydecane (110 g) were passed through a fixed-bed reactor heated at 350° C. and packed with 35 ml of catalyst B over a period of 4 hours under a pressure of 15 mbar. The effluent was condensed in a cold trap. Two phases formed on thawing. The methanol phase was separated and the other phase was distilled after the addition of a flake of KOH. There was obtained 1-methoxy-1-decene (68 g of cis/trans mixture) as a colorless liquid (bp 80° C./1 mbar) in a yield of 74%.

Example 23

1,1-Dimethoxydodecane (95 g) were passed through a fixed-bed reactor heated at 350° C. and packed with 35 ml of catalyst B over a period of 4 hours under a pressure of 12 mbar. The effluent was condensed in a cold trap. Two phases formed on thawing. The methanol phase was separated and the other phase was distilled after the addition of a flake of KOH. There was obtained 1-methoxy-1-dodecene (58 g of cis/trans mixture) as a colorless liquid (bp 100° C./1 mbar) in a yield of 72%.

We claim:

1. A process for the preparation of an enol ether of the general formula I

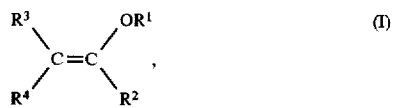

in which $R^1, R^2, R^3, R^4$ above and $R^5$ below denote $C_1$–$C_{20}$ alkyl, $C_1$–$C_{20}$ alkenyl, or $C_7$–$C_{20}$ phenylalkyl, $R^2, R^3, R^4$ denote hydrogen, aryl, cyano, —COOR$^5$, $C_1$–$C_{12}$ alkyl monosubstituted to trisubstituted or interrupted by —COOR$^5$, —C=O, cyano, or $C_1$–$C_{20}$ alkoxy, $C_1$–$C_{12}$ alkyl monosubstituted to trisubstituted by —COOR$^5$, —C=O, cyano, or $C_1$–$C_{12}$ alkyl, or $C_7$–$C_{20}$ phenylalkyl and $R^2$ and $R^4$ or $R^3$ and $R^4$ together form a $C_3$–$C_{10}$ alkylene chain or a $C_2$–$C_{20}$ alkylidene chain, from an acetal or ketal of the general formula II

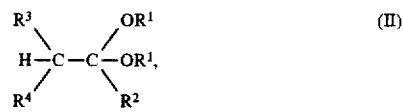

in which $R^1, R^2, R^3$, and $R^4$ have the aforementioned meanings and $R^1$ has the same meanings independently of $R^1$, in the gas phase at temperatures ranging from 100° to 550° C. and under a pressure of from 0.001 to 5 bar over a heterogeneous catalyst, which is a highly porous Group IIa, Group IIIa, Group IVa, Group IIb or Group IVb oxide, or a mixture thereof, having a pH of from 7 to 14, a porosity of from 40 to 80%, and a BET surface area of from 0.5 to 250 m²/g.

2. A process for the preparation of an enol ether I as defined in claim 1, wherein the reaction is carried out at temperatures ranging from 180° to 400° C.

3. A process for the preparation of an enol ether I as defined in claim 1, wherein the reaction is carried out at temperatures ranging from 200° to 350° C.

4. A process as claimed in claim 1, wherein the heterogeneous catalyst is a highly porous magnesium oxide, aluminum oxide, silicon dioxide, titanium oxide or a mixture thereof.

5. A process as claimed in claim 1, wherein the heterogeneous catalyst is a highly porous α-aluminum oxide, Γ-aluminum oxide, silicon dioxide, zinc oxide/Γ-aluminum oxide or a mixture thereof.

6. A process as claimed in claim 1, wherein the heterogeneous catalyst is a highly porous Γ-aluminum oxide, silicon dioxide or a mixture thereof having a pH of from 11 to 14.

7. A process as claimed in claim 1, wherein the heterogeneous catalyst is a highly porous α-aluminum oxide.

8. A process as claimed in claim 1, wherein the porosity of the heterogeneous catalyst is above 50%.

9. A process as claimed in claim 1, wherein the porosity of the heterogeneous catalyst is above 60%.

10. A process as claimed in claim 1, wherein the heterogeneous catalyst has a porosity of above 50% and a pH value of from 11 to 14, and the reaction is carried out at a temperature of from 180° to 400° C., a pressure of from 0.01 to 2 bar and optionally in the presence of an inert gas.

* * * * *

UNITED STATES PATENT AND TRADEMARK OFFICE
CERTIFICATE OF CORRECTION

PATENT NO. : 5,767,325
DATED : June 16, 1998
INVENTOR(S) : Schröder et al.

It is certified that error appears in the above-indentified patent and that said Letters Patent is hereby corrected as shown below:

Column 1, line 49: Between $R^4$ and $R^5$, cancel the comma "," and substitute the words --above and--; and after $R^5$, insert --below--; and before "alkenyl", cancel "$C_1-C_{20}$" and substitute --$C_2-C_{20}$--.

Column 1, lines 60-65: Correct the structure of the formula II to read:

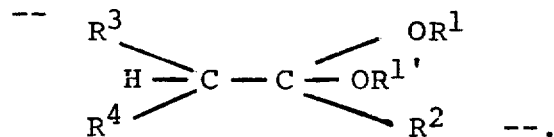

--.

Column 2, line 6: Before "surface", insert --BET--, and after "area", cancel "(BET)".

IN THE CLAIMS:

Claim 1, line 38 in column 9: Before "alkenyl", cancel "$C_1-C_{20}$" and substitute --$C_2-C_{20}$--.

Claim 1, line 41 in column 9: After "or", cancel "$C_1-C_{20}$" and substitute --$C_1-C_{12}$--.

UNITED STATES PATENT AND TRADEMARK OFFICE
CERTIFICATE OF CORRECTION

PATENT NO. : 5,767,325
DATED : June 16, 1998
INVENTOR(S) : Schröder et al.

It is certified that error appears in the above-identified patent and that said Letters Patent is hereby corrected as shown below:

Claim 1, lines 1-5 in column 10: Correct the structure of the formula II to show the $OR^{1'}$ as shown in the formula above.

Signed and Sealed this

Twenty-ninth Day of September, 1998

Attest:

BRUCE LEHMAN

*Attesting Officer*  *Commissioner of Patents and Trademarks*